US007294846B2

(12) United States Patent
Pedersen

(10) Patent No.: US 7,294,846 B2
(45) Date of Patent: Nov. 13, 2007

(54) APPARATUS AND A METHOD OF DETECTING HYDROGEN IN AN OBJECT BY USE OF A NEUTRON

(75) Inventor: Niels Hald Pedersen, Hvidovre (DK)

(73) Assignee: Force Technology, Brondby (DK)

( * ) Notice: Subject to any disclaimer, the term of this patent is extended or adjusted under 35 U.S.C. 154(b) by 17 days.

(21) Appl. No.: 10/539,709

(22) PCT Filed: Dec. 19, 2003

(86) PCT No.: PCT/DK03/00909

§ 371 (c)(1),
(2), (4) Date: Jan. 17, 2006

(87) PCT Pub. No.: WO2004/057318

PCT Pub. Date: Jul. 8, 2004

(65) Prior Publication Data

US 2006/0108535 A1    May 25, 2006

(30) Foreign Application Priority Data

Dec. 20, 2002    (DK) ............................... 2002 01961

(51) Int. Cl.
*G01N 21/86* (2006.01)
(52) U.S. Cl. .................... 250/559.4; 250/221
(58) Field of Classification Search ............ 250/559.4, 250/221, 559.21, 390.01, 390.05, 390.11, 250/370.05, 370.11, 393
See application file for complete search history.

(56) References Cited

U.S. PATENT DOCUMENTS 3,707,631 A    12/1972 Untermyer 4,499,380 A *  2/1985 Aggour et al. ......... 250/390.04
5,446,288 A    8/1995 Tumer

FOREIGN PATENT DOCUMENTS

| GB | 984 566 | 9/1961 |
|---|---|---|
| GB | 1 058 775 | 11/1963 |
| GB | 1 180 450 | 3/1967 |
| WO | WO 02/31536 | 4/2002 |

OTHER PUBLICATIONS

Patent Abs. of Japan vol. 1999, No. 05, May 31, 1999 & JP 11 051799 A—Chisaka Haruo).
Patent Abs. of Japan vol. 009, No. 006 Jan. 11, 1985 & JP 59 154347—Soiru Ando Rotsuku Engineering KK.

* cited by examiner

*Primary Examiner*—Que T Le
(74) *Attorney, Agent, or Firm*—Day Pitney LLP

(57) ABSTRACT

This invention relates to an apparatus for the detection of the hydrogen content of an object, wherein said apparatus comprises a neutron source that emits fast/energy-rich neutrons; a detector device for detecting thermal neutrons; a moderator that brakes and reflects neutrons upon collision; wherein said detector device comprises a light-emitting unit that emits light in case of a nuclear event/reaction with a thermal neutron; a light-registering unit that emits an electric pulse/an electric signal when a flash of light is detected; and wherein said moderator is a light-conductive unit arranged between said light-emitting unit and said light-registering unit. Moreover the invention relates to a corresponding method of detecting hydrogen. Hereby an apparatus and a method are provided for the detection of humidity/water/hydrogen with improved sensitivity which entails that the used neutron source need not be as powerful and that smaller amounts of hydrogen can be detected compared to previously suggested solutions. Moreover, a reliable non-modifying/non-destructive detection is provided.

14 Claims, 2 Drawing Sheets

APPARATUS AND A METHOD OF DETECTING HYDROGEN IN AN OBJECT BY USE OF A NEUTRON

FIELD OF THE INVENTION

This invention relates to an apparatus for detecting the contents of hydrogen in an object.

This invention also relates to a method of detecting the contents of hydrogen in an object.

BACKGROUND OF THE INVENTION

In general, the invention relates to a detection apparatus that is able to detect hydrogen (for instance for detecting an amount of water) in an object by use of a neutron source. A neutron source for this purpose presents the advantage in that neutrons are able to penetrate certain barriers. For instance, it is possible by this invention to estimate the amount of hydrogen, water and/or humidity in, for example, insulation material arranged in a steel pipe. It can be used for checking whether and how much water/humidity there is present in the insulation material, which is important to know, for example, in connection with the assessment of the risk of corrosion, rust, etc. This may be performed without having to remove or cut in parts of the pipe/object or to separate the object/pipe or parts thereof.

A source of fast neutrons emits fast/energy-rich neutrons, therefore neutrons with high kinetic energy. In the present invention the known discovery is used to advantage that atomic nuclei (and in particular hydrogen) brake neutrons upon collision, a phenomenon typically referred to as elastic scattering/collision (whereby the velocity is reduced and the direction is changed for a collided neutron). This invention uses a detector device that detects relatively slow/energy-poor neutrons, the so-called thermal neutrons. After a neutron has been braked sufficiently, it can be detected by the detector device. The process of braking neutrons is typically designated 'moderation' and a physical arranged for this a 'moderator'. In order for a neutron to be detected, most often is has to collide several times with hydrogen atoms.

In order to accomplished an increased sensitivity it is known to configure the detection apparatus to comprise an (auxiliary) moderator, an amount of hydrogen or a moderator material that brakes and reflects/scatters neutrons by elastic scattering/collision and is arranged such that a portion of incoming neutrons are reflected against the detector and the hydrogen for detection. In broad outline the further amount of hydrogen/moderator material serves as a (partial) neutron reflector that also brakes the neutrons, thereby causing a larger amount of braked/thermal neutrons to be detected. This is also often referred to as neutron back-scatter.

Patent specification GB A 1180450 discloses an arrangement for detecting humidity/hydrogen by use of a neutron source. The arrangement according to GB A 1180450 is shown schematically in FIG. 1 and comprises a fast-neutron source (103), a detector for thermal neutrons (102) and a hydrogen-containing neutron-braking and -reflecting/-scattering material (therefore moderator material) (104) for providing the back-scatter effect, wherein the detector (102) and the source (103) are arranged between this material (104) and the material/object (101) in which the humidity/water/hydrogen is to be detected.

It is mentioned in patent specification GB A 1180450 that the detector of thermal neutrons (102) may be a scintillator.

Albeit the detector according to GB A 1180450 has an increased sensitivity due to the moderator (104), it is possible to accomplish superior sensitivity as taught by the present invention.

Patent specification U.S. Pat. No. 3,707,631 relates to a system for non-destructive analysis of nuclear fuel, wherein a neutron source and a detector device are arranged to each their side of the sample. The source emits low-energy neutrons (<1 Mev), therefore not thermal, where a comparatively large moderator brakes the emitted neutrons to the effect that they can initiate a fission process that emits fast (>1 Mev) neutrons that are detected in an energy-selective scintillator. In this system, measurement is performed on fast neutrons and various measures must be taken to separate them from the (almost equally) fast neutrons from the source that have not been braked. A light guide is also mentioned, the primary function of which is to couple a number of very different scintillator geometries to the front of a standard photo-multiplier.

The arrangement disclosed in U.S. Pat. No. 3,707,631 is not directed against or suitable for the detection of hydrogen.

Patent specification No. U.S. Pat. No. 5,446,288 teaches detection of hydrogen and other light elemental substances using detection of when thermal neutrons, where light source and detector are on the same side of the sample. A detector device comprises a scintillator coupled to a photo-multiplier via a light guide in the form of an air light guide, wherein the neutron source is enclosed by moderator material that is separated from the light guide.

SUMMARY OF THE INVENTION

It is an object of the invention to provide an apparatus for the detection of humidity/water/hydrogen and exhibiting improved sensitivity.

It is a further object of the invention to provide a detection apparatus, wherein the strength of the used neutron source need not be as powerful as in the prior art.

It is a further object of the invention to provide a detection apparatus with reliable, non-modifying/non-destructive detection.

It is also an object of the invention to provide a compact detection apparatus.

These objects are provided by an apparatus of the kind described above and comprising:
 a neutron source that emits fast/energy-rich neutrons;
 a detector device for detecting thermal neutrons;
 a moderator that brakes and reflects neutrons upon collision;

wherein
 said detector device comprises
  a light-emitting unit that emits light in case of a nuclear event/reaction with a thermal neutron; and
  a light-registering unit that emits an electric pulse/an electric signal when a flash of light is detected; and
 said moderator is a light-conductive unit arranged between said light-emitting unit and said light-registering unit.

Hereby a hydrogen-detector/humidity probe is achieved that features improved sensitivity, the light-conductive unit providing a conductivity/concentration of the light from the light-emitting unit to the light-registering unit, thereby further improving the performance/sensitivity, as it is ensured that all nuclear events that bring about a flash of light will, with a much increased degree of reliability, be registered by the light-registering unit.

Moreover, the dual function of the light-conductive unit, as it also provides a moderating effect, therefore contains hydrogen/moderator material for accomplishing the abovementioned back-scatter effect, means that the apparatus according to the invention can be configured to be compact or at least not with dimensions that exceed the solutions that already comprise an auxiliary moderator.

The increased sensitivity means that the used neutron source need not be so powerful as to constitute a health risk and thus presupposes safety equipment for an operator or cumbersome handling thereof, while simultaneously a reliable, non-modifying/non-destructing detection is still provided, therefore without modification of a measurement object (for example, sampling, cutting off a part of a pipe/object, taking it apart, etc). Moreover, smaller amounts of hydrogen can be detected compared to previously known solutions, due to the increased sensitivity.

According to one embodiment, said light-emitting unit is a scintillator and said light-registering unit is a photomultiplier (PM)).

Alternatively the light-registering unit is a photo-diode.

According to one embodiment, said source is comprised of or embedded in said moderator. Hereby a compact detector is provided.

According to a preferred embodiment said light source is arranged essentially in proximity of or in/around the centre of the face of said moderator that adjoins the light-emitting unit.

This position has proved to be convenient in order to accomplished further enhanced sensitivity, as a larger amount of neutrons will be reflected and moderated and hence detected.

According to one embodiment said light-conductive unit is configured essentially with a face that adjoins said light-emitting unit and having a relatively smaller face adjoining a detection face of said light-registering unit.

Hereby a comparatively larger face of the light-emitting unit can be coupled optically to a smaller detection face of the light recording unit, which yields an advantage with regard to economics, the cost of such light-registering units being relatively high and depending to a large extent on the recording area.

For instance, said light-conductive unit may be configured essentially as a cone, where the top is cut way (therefore, a trapezoidal shape in 2D/in case of a section in the centre line of the cone as indicated, for example, in FIG. 2a).

In one embodiment, said light-conductive unit is configured for emitting light conducted from said light-emitting unit to the light-registering unit essentially perpendicular to a detection face of the apparatus.

Hereby a detection apparatus is readily provided that has a larger expanse essentially perpendicular to a detection face of the object in which hydrogen is to be detected. This gives an advantageous embodiment, in particular if the detection apparatus according to the invention is intended for being operated primarily in a depth/in a longitudinal direction.

According to an alternative embodiment said light-conductive unit is configured for emitting light conducted from said light-emitting unit to the light-registering unit essentially in parallel with a detection face of the apparatus.

In this manner a detection apparatus is readily provided that has a larger expanse, essentially in parallel with a detection face of the object in which hydrogen is to be detected. In popular terms the detection apparatus is longer than it is wide. Hereby an advantageous configuration is provided, in particular if the detection apparatus according to the invention is intended for being handheld and operated manually.

According to one embodiment the apparatus further comprises an electric circuit connected to said detector device, wherein said circuit is configured for generating a signal that represents an estimated amount of hydrogen, water and/or humidity content on the basis of the electric signal from said light-registering unit.

Moreover the invention relates to a method of detecting hydrogen content of an object comprising the steps of:
  emitting fast/energy-rich neutrons from a neutron source;
  detecting thermal neutrons by means of a detector device;
  braking and reflecting neutrons by collision of a moderator, wherein the method further comprises:
  emitting light by a light-emitting unit by a nuclear event/reaction with a thermal neutron;
  emitting an electric pulse/an electric signal by a light-registering unit upon recording of a flash of light; and
  conducting light from said light-emitting unit to said light-registering unit by a light-conductive unit arranged between said light-emitting unit ands said light-registering unit; of which said moderator is the light-conductive unit.

According to one embodiment said light-emitting unit is a scintillator and said light-registering unit is a photomultiplier (PM) or a photo-diode.

According to one embodiment said source is comprised of or embedded in said moderator. Hereby compact detection is provided.

According to one embodiment said source is arranged essentially in proximity of or about/in the centre of the face of said moderator that adjoins the light-emitting unit.

According to one embodiment, said light-conductive unit is configured essentially with a face adjoining said light-emitting unit and having a relatively smaller face adjoining a detection face of said light-registering unit.

According to one embodiment said light-conductive unit is configured for emitting light conducted from said light-emitting unit to the light registering unit essentially perpendicular to a detection face.

According to one embodiment said light-conductive unit is configured for emitting light conducted from said light-emitting unit to the light-registering unit essentially in parallel with a detection face.

According to one embodiment the method further comprises generation within an electric circuit connected to said detector unit a signal representing an estimated amount of hydrogen, water and/or humidity content, wherein said generation is performed on the basis of the electric signal from said light-registering unit.

The method according to the invention and embodiments thereof correspond to the apparatus according to the invention and embodiments thereof and have the same effects for the same reasons.

In the following the invention will be explained in further detail with reference to the drawing, wherein

DETAILED DESCRIPTION OF THE INVENTION

Figure 1:
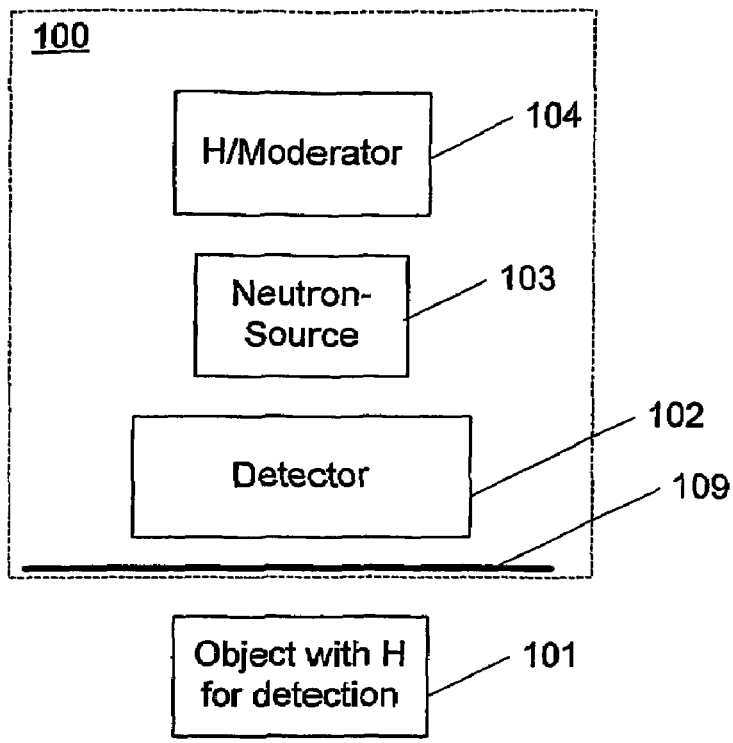
FIG. 1 illustrates prior art that uses the back-scatter principle for detecting hydrogen/water.

FIG. 1 illustrates the prior art that uses the back-scatter priciple for detecting hydrogen/water. Shown is a detection apparatus (100) for detecting hydrogen in an object (101). The detection apparatus (100) comprises a moderator containing hydrogen (104), a fast-neutron source (103), and a detector for thermal neutrons (102), wherein the neutron source (103) and the detector for thermal neutrons (102) are arranged between the moderator (104) and the object (101) by use of a detection apparauts (100). Moreover a detectin face (109) for the detection apparatus (100) is shown schematically, therefore the face to be arranged adjoining the object (101) in which hydrogen is to be detected. Neutrons emitted by the source (103) will have largely all directions, and some of these neutrons will collide with the hydrogen both in the moderator (104) and with the hydrogen that is to be estimated in the object (101), whereby the neurtons will change direction and loose speed. A portion of the neutrons will be reflected against the detector by thermal neutrons 102, and when they have collided sufficiently many time they will be thermal (therefore they will typically have a kinetic energy within the range of about approximately 0.025 eV), whereby the detector will record them, and the amount of hydrogen in the object (101) can be detected. Some neutrons will be reflected both by the moderator (104) and the hydrogen in the object (101), while others will continue in other directions an/or be absorbed. Typically a neutron shall collide in average six time with a hydrogen atom in order to have an energy that the detector is able to detect (the neutron needs to reduce it energy level by approximately 6 to 8 orders of magnitude). The moderator (104) provides the effect that more neutrons with a suitable energy will be detected compared to a scenario in which it was only the hydrogen in the test object (101) that was primarily present for reducing the kinetic energy of the neutrons. Hereby the sensitivity of the detection apparatus (100) is enhanced.

Figure 2A:
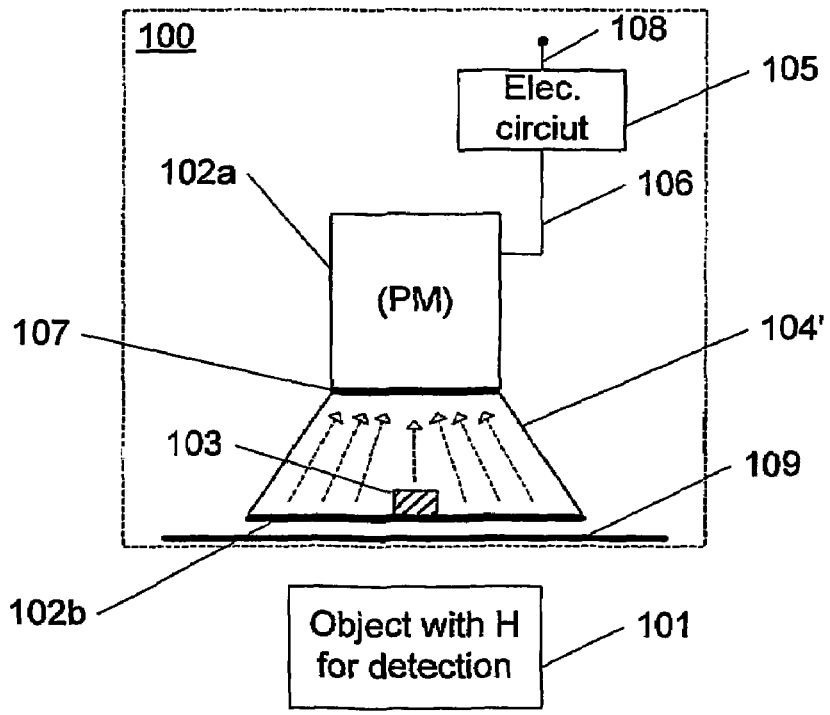
FIG. 2a schematically illustrates an embodiment of an apparatus according to the invention.

FIG. 2a schematically illustrates an embodiment of an apparatus according to the invention. Shown in the figure is a detection apparatus (100) that comprises a neutron source (103) and neutron-braking and -reflecting material (104'), therefore moderator material, for example, comprising hydrogen. The detection apparatus (100) has a detection face (109) that is intended for being directed towards or against an object (101) in which hydrogen is to be detected.

Moreover the detection apparatus (100) comprises a detector of thermal neutrons (102a, 102b) that comprises, in accordance with the invention, a light-emitting unit (102b) and a light-registering unit (102a), wherein the light registering unit (102a) is connected to an electric circuit (105). The light-emitting unit (102b) emits light by a nuclear event/reaction with a thermal neutron, while the light-registering unit (102a) emits an electric pulse/an electric signal (106) upon registration of a flash of light, where the emitted electric pulse/the emitted electric signal is received in the electric circuit (105) for subsequent interpretation, processing, etc.

According to the invention the moderator material is a light-conductive unit or a light-conductive material (104'). In this manner the light-conductive unit (104) comprises both a moderating effect, therefore contains hydrogen/moderator material for obtaining the above-referenced back-scatter effect, and conducting/concentrating light from the light-emitting unit (102b) to the detection face (107) of the light-registering unit (102a), thereby further enhancing the performance/sensitivity, it being ensured that all nuclear events that bring about a flash of light will; with a much higher degree of certainty, be recorded by the light-registering unit (102a), thereby enabling that smaller amounts of hydrogen can be detected without an ensuing need to increase the strength of the neutron source.

The movement of the light from the light-emitting unit (102b) to the light-registering unit (102a) is shown schematically by dotted arrows in the figure.

Moreover the dual function of the light-conductive unit/moderator (104') means that the detection apparatus (100) can be configured compact or at least not larger than solutions that already comprise an auxiliary moderator for achieving neutron back-scatter.

In the shown embodiment the light-conductive unit (104') is configured essentially with a face adjoining said light-emitting unit (102b) and having a relatively smaller face adjoining a detection face (107) of the light-registering unit (102a).

Hereby a relatively larger face of the light-emitting unit (102b) can be coupled optically to a smaller detection face (107) of the light-registering unit (102a), which yields an advantage from a financial point of view, as the price of such light-registering units (102a) is comparatively high and to a large degree depend on the registration area.

For instance, the light-conductive unit can be configured essentially as a cone, where the top is cut away (therefore a trapezoidal form in 2D/in case of a section in the centre line of the cone, for example, as shown in the drawing).

The light-conductive unit/the light-conductive material (104') may, for example, be a light-guide (English term) comprising hydrogen and/or other moderator material. According to a preferred embodiment the light-guiding unit/the light conductive material (104') comprises Plexiglas.

Preferably the neutron source is comprised of/embedded in said moderator (104') and arranged essentially around or in the centre of the face of said moderator (104') that adjoins the light-emitting unit (102b).

This arrangement has proven to be convenient in order to obtain enhanced sensitivity as a larger number of neutrons will be reflected and moderated and hence detected.

According to one embodiment the light-emitting unit (102a) is a scintillator, which is a known standard unit that records a nuclear event and emits a flash of light when, for example a thermal neutron hits the scintillator (102b). In practice photons are released. One example of a scintillator (102b) includes glass enriched with the lithium isotope Li-6.

According to one embodiment the light-emitting unit (102b) is a photo-multiplier, which is also a known standard unit that records even very weak flashes of light/photons and generates an electric pulse on the background of one or more of such. Alternatively the light-registering unit (102a) is a photo-diode.

The electric circuit (105) receives electric pulses/signals from the light-registering unit/photo-multiplier (102a) and is thus able to record and/or process these signals depending on the relevant use, for example, for estimating the amount of water/humidity/hydrogen in the object (101) or for other applications. For instance, one or more electric output signals (108) from the electric circuit (105) can be used, for example, for a display/meter (not shown) that shows the estimated amount and/or other functions.

Moreover the detection apparatus (100) may comprise other types (optionally non-hydrogen-containing materials) of light-conductive material (104') as long as they have a neutron-moderating effect.

Preferably the light-registering unit/photo-multiplier (102a) and the light guide (104) will collide/adjoin each other at the detection face (107) of the light-registering unit/the photo-multiplier with an optical adaptor material there between, such as, for example, silicon grease, transparent silicon, joint filler, etc. to ensure as low an optic loss as possible by the transition.

The neutron source (103) may be, for example, an isotope-based neutron source.

Alternatively the neutron source (103) can also be arranged elsewhere than within/around the centre of the light guide (104').

The electric circuit (105) may have many functions and configurations depending on the current use of the invention. A simple electric circuit merely has to record the number of electric pulses from the photo-multiplier/the light-registering unit (102a) for a period of time in order to be able to estimate the amount of water/hydrogen in a simple manner. Alternatively more sophisticated electric circuits can be used.

Moreover the apparatus (100) may comprise a material disc, plate, piece, etc (not shown) arranged such that the neutron source (103) is between that and the detection face (109). Said disc, plate, piece, etc, must be of a material that possesses the property that it is good at reflecting neutrons without considerable loss of energy, for example, iron or molybdenum. Moreover the apparatus (100) may comprise a ring, pipe, cylinder, etc, arranged such that it encircles the neutron source (103), whereby gamma radiation, if any, is removed that may otherwise give false hits upon reaction with the light-emitting unit (102b). This ring, pipe, cylinder, etc, has to be of a material that possesses the property that, to a particular extent, it absorbs gamma radiation, for example, lead or wolfram.

Figure 2B:
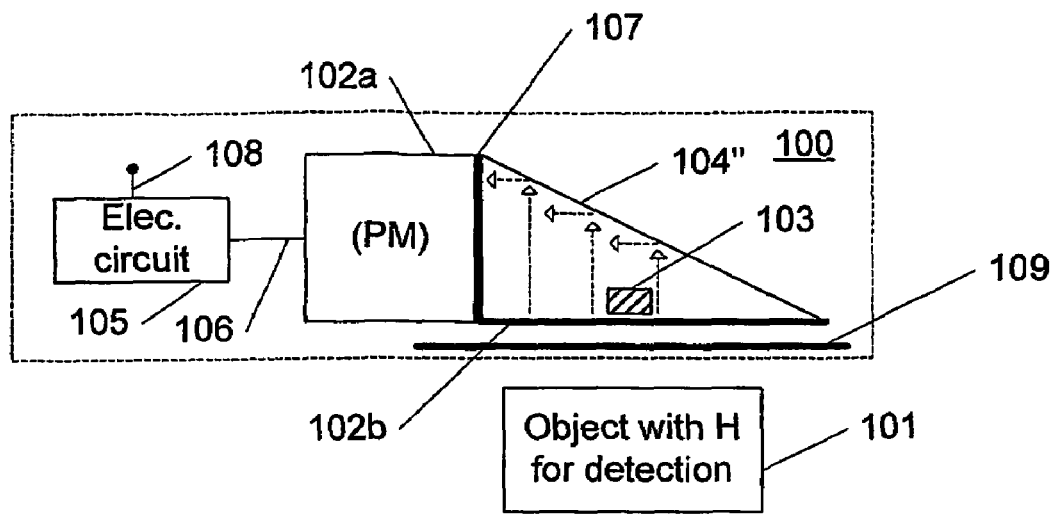
FIG. 2b schematically illustrates an embodiment of an apparatus according to the invention.

FIG. 2b schematically illustrates an alternative embodiment of an apparatus according to the invention. Shown in the figure is a detection apparatus (100) according to the invention comprising the same elements/units as shown in and explained in connection with FIG. 2a, but wherein they are arranged and optionally configured differently. More specifically the combined moderator and light-conductive unit (104") is configured such that it essentially conducts the light in parallel with the detection face (109) of the detection apparatus (100) to the light-registering unit (102a) (conversely to the embodiment shown in FIG. 2a, where the light is conducted essentially perpendicular to the detection face (109), thereby enabling a rather elongate configuration of the detection apparatus (100). The light-conductive unit (104") may be configured, for example, as shown in the figure, with a 2D profile as a triangle, wherein the incoming light from the light-emitting unit (102b) is reflected essentially perpendicular in relation to the incoming direction, therefore essentially in parallel with the detection face (109).

Alternatively the light-conductive unit (104") may be a batch of optical fibres/optical fibre cable that angles/turns/deflects the light sideways in relation to the primary angle of incidence, therefore essentially in parallel with the detection face (109).

The movement of the light from the light-emitting unit (102b) to the light-registering unit (102a) is shown schematically by dotted arrows in the figure.

In the shown embodiment, the light-conductive unit (104") is configured essentially with a face adjoining said light-emitting unit (102b) and having a relatively smaller face adjoining a detection face (107) of the light-registering unit (102a).

The elongate configuration is particularly useful if the detection apparatus (100) is to have a configuration that is suitable for handheld/manual operation with ensuing easier handling/operation.

Figure 2C:
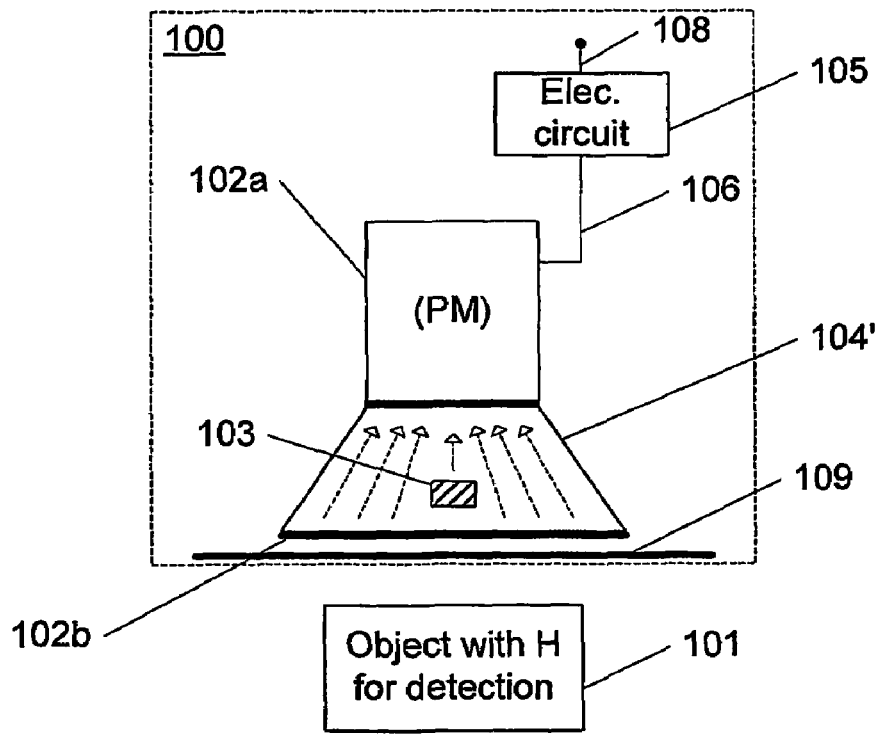
FIG. 2c schematically illustrates an alternative embodiment of an apparatus according to the invention.

FIG. 2c schematically illustrates an alternative embodiment of an apparatus according to the invention. The shown embodiment corresponds to the one shown in FIG. 2a, but wherein the location of the neutron source (103) is changed. In the shown embodiment the neutron source (103) is arranged more towards the centre of the moderator (104"), therefore not in the face of the moderator (104") that adjoins the light-emitting unit (102b). Alternatively, the neutron source (103) can be arranged, for example, more towards the sides of the moderator (104"). The same modification of the position of the neutron source can also be performed in the embodiment shown in FIG. 2b or others.

The invention claimed is:

1. An apparatus for detecting the hydrogen content of an object (101), wherein the apparatus (100) comprises
    a neutron source (103) that emits fast/energy-rich neutrons;
    a detector device (102; 102a; 102b) for detecting thermal neutrons;
    a moderator (104; 104'; 104") that brakes and reflects neutrons upon collision; characterised in that
    said detector device comprises
        a light-emitting unit (102b) that emits light in case of a nuclear event/reaction with a thermal neutron; and
        a light-registering unit (102a) that emits an electric pulse/an electric signal (106) when a flash of light is detected;
    said moderator (104', 104") is a light-conductive unit arranged between said light-emitting unit (102) and said light-registering unit (102a); and
    said neutron source (103) is embedded in said moderator (104').

2. An apparatus according to claim 1, characterised in that said light-emitting unit (102b) is a scintillator and that said light-registering unit (102a) is a photo-multiplier (PM) or a photo-diode.

3. An apparatus according to claim 1, characterised in that said source (103) is arranged essentially in proximity of or about/in the centre of the face of said moderator (104', 104") that adjoins the light-emitting unit (102b).

4. An apparatus according to claim 1, characterised in that said light-conductive unit (104') is configured essentially with a face that adjoins said light-emitting unit (102b) and having a relatively smaller face adjoining a detection face (107) of said light-registering unit (102a).

5. An apparatus according to claim 1, characterised in that said light-conductive unit (104") is configured for emitting light conducted from said light-emitting unit (102b) to the light-registering unit (102a) essentially perpendicular to a detection face (109) of the apparatus (100).

6. An apparatus according to claim 1, characterised in that said light-conductive unit (104") is configured for emitting light conducted from said light-emitting unit (102b) to the light-registering unit (102a) essentially in parallel with a detection face (109) of the apparatus (100).

7. An apparatus according to claim 1, characterised in that the apparatus further comprises an electric circuit (105) connected to said detector device (102; 102a), wherein said circuit (105) is configured for generating a signal (108) that represents an estimated amount of hydrogen, water and/or humidity content on the basis of the electric signal (106) from said light-registering unit (102*a*).

8. A method of detecting the hydrogen content (101) of an object comprising the steps of:
- emitting fast/energy-rich neutrons from a neutron source (103);
- detecting thermal neutrons by means of a detector device (102; 102*a*; 102*b*);
- braking and reflecting neutrons by collision with a moderator (104; 104'; 104"), characterised in that the method further comprises:
- emitting light by a light-emitting unit (102*b*) in the event of a nuclear event/reaction with a thermal neutron;
- emitting an electric pulse/an electric signal (106) by a light-registering unit (102*a*) upon recording of a flash of light;
- conducting light from said light-emitting unit (102*b*) to said light-registering unit (102*a*) by a light-conductive unit arranged between said light-emitting unit (102*b*) and said light-registering unit (102*a*); of which said moderator (104'; 104") is the light-conductive unit, where said neutron source (103) is embedded in said moderator (104').

9. A method according to claim 8, characterised in that said light-emitting unit (102*b*) is a scintillator and that said light-registering unit (102*a*) is a photo-multiplier (PM) or a photo-diode.

10. A method according to claim 8, characterised in that said source (103) is arranged essentially in proximity of or around/in the centre of the face of the moderator (104', 104") that adjoins the light-emitting unit (102*b*).

11. A method according to claim 8, characterised in that said light-conductive unit (104') is configured essentially with a face that adjoins said light-emitting unit (102*b*) and having a relatively smaller face adjoining a detection face (107) of said light-registering unit (102*a*).

12. A method according to claim 8, characterised in that said light-conductive unit (104") is configured for emitting light conducted from said light-emitting unit (102*b*) to the light-registering unit (102*a*) essentially perpendicular to a detection face (109).

13. A method according to claim 8, characterised in that said light-conductive unit (104") is configured for emitting light conducted from said light-emitting unit (102*b*) to the light-registering unit (102*a*) essentially in parallel with a detection face (109).

14. A method according to claim 8, characterised in that the method further comprises generation, in an electric circuit (105) connected to said detector device (102; 102*a*), of a signal (108) representing an estimated amount of hydrogen, water and/or humidity content, wherein said generation is performed on the basis of the electric signal (106) from said light-registering unit (102*a*).

* * * * *